(12) United States Patent
Takahashi

(10) Patent No.: US 6,322,497 B1
(45) Date of Patent: Nov. 27, 2001

(54) ELECTRONIC ENDOSCOPE

(75) Inventor: Tadashi Takahashi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/471,380

(22) Filed: Dec. 23, 1999

(30) Foreign Application Priority Data

Dec. 25, 1998 (JP) .................................................. 10-370172

(51) Int. Cl.⁷ .................................................. A61B 1/045
(52) U.S. Cl. .............................. 600/118; 600/168; 348/65; 348/72
(58) Field of Search .................................... 600/109, 117, 600/128, 160, 168; 348/65, 72, 74, 583, 600

(56) References Cited

U.S. PATENT DOCUMENTS

| | | | |
|---|---|---|---|
| 4,841,363 | * 6/1989 | Arms et al. | 348/74 |
| 5,305,098 | * 4/1994 | Matsunaka et al. | 348/65 |
| 5,412,478 | * 5/1995 | Ishihara et al. | 348/72 |
| 5,871,439 | 2/1999 | Takahashi et al. | |

* cited by examiner

Primary Examiner—John Mulcahy
(74) Attorney, Agent, or Firm—Greenblum & Bernstein, P.L.C.

(57) ABSTRACT

An electronic endoscope of the present invention includes a video-scope having an image sensor, a video-processor, to which a proximal end of the video-scope and a monitor are respectively connected, a character and mark generation controller, and an area-image changer. The character and mark generation controller generates character signals and indicator-mark signals, and then feeds the character signals and the indicator-mark signals to the monitor. The image-area changer changes a size of an image-area of the object image displayed on the screen of the monitor to another size, thus the object image is selectively displayed within one of plural image-areas on the screen in accordance with a size change of the image-area. The characters and mark generation controller includes a display-position adjuster that determines display-positions of the character information and the indicator-mark on the basis of a reference table, in which a correspondence relationship between each of the image-area and each of the display-positions of the character information and the indicator-mark is indicated.

19 Claims, 12 Drawing Sheets

FIG. 4

| Scope Type | NORMAL | | | | MAGNIFICATION | | | | NORMAL | | | | MAGNIFICATION | | | |
|---|---|---|---|---|---|---|---|---|---|---|---|---|---|---|---|---|
| | A | | | | A | | | | B | | | | B | | | |
| | vs→ | 1 | 2 | | 3 | 4 | | | 5 | 6 | | | 7 | 8 | | |
| ITEM | cp | x | y | | x | y | | | x | y | | | x | y | | |
| NAME | 1 | 1 | 1 | | 0 | 0 | | | 1 | 1 | | | 0 | 0 | | |
| ID No. | 2 | 24 | 1 | | 1 | 1 | | | 24 | 1 | | | 0 | 1 | | |
| AGE | 3 | 24 | 2 | | 5 | 3 | | | 24 | 2 | | | 3 | 3 | | |
| SEX | 4 | 29 | 2 | | 3 | 4 | | | 29 | 2 | | | 3 | 4 | | |
| Dr.NAME | 5 | 24 | 13 | | 0 | 28 | | | 24 | 13 | | | 0 | 28 | | |
| SCOPE-NAME | 6 | 26 | 21 | | 0 | 31 | | | 26 | 21 | | | 0 | 31 | | |
| DATE | 7 | 24 | 9 | | 35 | 29 | | | 24 | 9 | | | 26 | 30 | | |
| TIME | 8 | 26 | 10 | | 36 | 31 | | | 26 | 10 | | | 27 | 31 | | |
| $A_{min}$ | 9 | 0 | 2 | | 8 | 1 | | | 3 | 3 | | | 5 | 0 | | |
| $A_{max}$ | 10 | 18 | 23 | | 34 | 30 | | | 21 | 22 | | | 29 | 30 | | |

T

ELECTRONIC ENDOSCOPE

BACKGROUND OF THE INVENTION

1. Field of the Invention

This invention relates to an electronic endoscope for displaying a body-cavity image on a TV monitor, the endoscope having a video-scope having an image sensor and a video-processor. In particular, this invention relates to an adjustment of display-positions of character information including a patient's name, displayed on the monitor with the body-cavity image.

2. Description of the Related Art

In an electronic endoscope, a video-scope includes an optical light guide extended therethrough, which is formed as a bundle of optical fibers. A video-processor includes a light source, such as a halogen lamp. When the video-scope is connected to the video-processor, a proximal end of the optical light guide is optically connected to the light source. Thus, an object to be photographed is illuminated by light radiating from a distal end of the optical light guide, and then an object image is formed on a CCD (Charge-Coupled-Device) provided at the distal end of the video-scope, which is an image sensor. The object image, formed on the CCD, is converted into analog image-pixel signals by photoelectric conversion. The analog image-pixel signals are fed to the video-processor and are suitably processed, so that video signals are generated. The video signals are then output to a TV monitor. Thus, a body-cavity image (for example, an image of a stomach) is displayed on the monitor.

Further, a CRT controller for generating character signals is incorporated in the video-processor. Thus, character information, such as a patient's name and a doctor's name, and a pointer for pointing to a specific portion of the cavity can be also displayed on the monitor with the body-cavity image.

As is well known, the CCD in the video-scope has a smaller size than that of a CCD used in a normal camera. Namely, a number of image pixels, included in one frame, obtained from the video-scope CCD, is less than a number of image pixels, included in one frame, obtained from the normal camera CCD. Therefore, the object image, formed on the CCD in the video-scope, is only displayed on a partial area of the screen of the monitor. Accordingly, in a conventional electronic endoscope, a size of the image-area, within which the object image is displayed, is selectively and optionally changeable when a detailed examination of the diseased portion in the organ is needed. Thus, the object image, displayed on the screen, is enlarged to a predetermined size. Also, a large-sized image-area can be returned to the original-sized image-area.

In accordance with the size-change of the image-area, the character information is also shifted. Namely, a display-position of each item of the character information is changed such that the character information does not overlap the image-area on the screen. A display-position of the pointer is changed only when the pointer is displayed beyond the image-area by the size-change of the image-area.

A control process for changing the displayed-positions of the character information and the pointer is performed under a program in the video-processor. In a source code of the program, which is made by using a programming language, such as the "C" programming language, a description for computing the display-positions corresponding to each item of the character information and the original-sized/the large-sized image-area is needed.

However, the size of the image-area, within which the object image is displayed on the screen, differs from one video-scope to another because of differing characteristics of the CCDs in the video-scopes. Further, a hospital name, a patient's registration number and a patient's sex, and etc., should be also displayed on the screen with the patient's name and age. Therefore, the description for determining the display-positions in the source code increases as the kinds of video-scopes and the amount of character information increases. As a consequence, the structure of the source code becomes complicated, and processing for displaying of the character information cannot be rapidly performed.

Then, as inspection of the source code is difficult, reliability of operation of the electronic endoscope as a whole decreases. Further, the capacity of a memory, in which the program is stored, cannot be reduced.

SUMMARY OF THE INVENTION

Therefore, an object of the present invention is to provide an electronic endoscope that can execute a processing for displaying the character information and the pointer in accordance with a size-change of the image-area by a simple program.

An electronic endoscope of the present invention has a video-scope having an image sensor, a video-processor, to which a proximal end of the video-scope and a monitor are respectively connected, a character and mark generation controller, and an image-area changer.

In the video-scope, an object image is formed on the image sensor provided at a distal end of the video-scope, and then image-pixel signals corresponding to the object image are generated. In the video-processor, image-pixel signals are processed and video signals are generated to display the object image on the monitor. The character and mark generation controller generates character signals and indicator-mark signals, and then feeds the character signals and the indicator-mark signals to the monitor at a timing, such that character information and an indicator-mark are respectively displayed at a position on a screen of the monitor with said object image. The image-area changer changes a size of an image-area of the object image displayed on the screen of the monitor to another size, thus the object image is selectively displayed within one of plural image-areas on the screen in accordance with a size-change of the image-area.

Further, the character and mark generation controller includes a display-position adjuster. The display-position adjuster determines display-positions of the character information and the indicator-mark on the basis of a reference table, in which correspondence between each of the image-areas and each of the display-positions of the character information and the indicator-mark is indicated. Thus, the character information and the indicator-mark are respectively displayed at the determined display-positions in accordance with the size-change of the image-area.

As the display-positions of the character information and the indicator-mark are determined on the basis of the reference table, the structure of the program is simple. Therefore, the reliability of the operation of the electronic endoscope improves, and further, the program can be stored in a reduced-capacity memory.

BRIEF DESCRIPTION OF THE DRAWINGS

The present invention will be better understood from the description of the preferred embodiment of the invention set forth below together with the accompanying drawings, in which:

FIG. 4 is a view showing a reference table.

DESCRIPTION OF THE PREFERRED EMBODIMENTS

Hereinafter, the preferred embodiment of the present invention is described with reference to the attached drawings.

Figure 1:
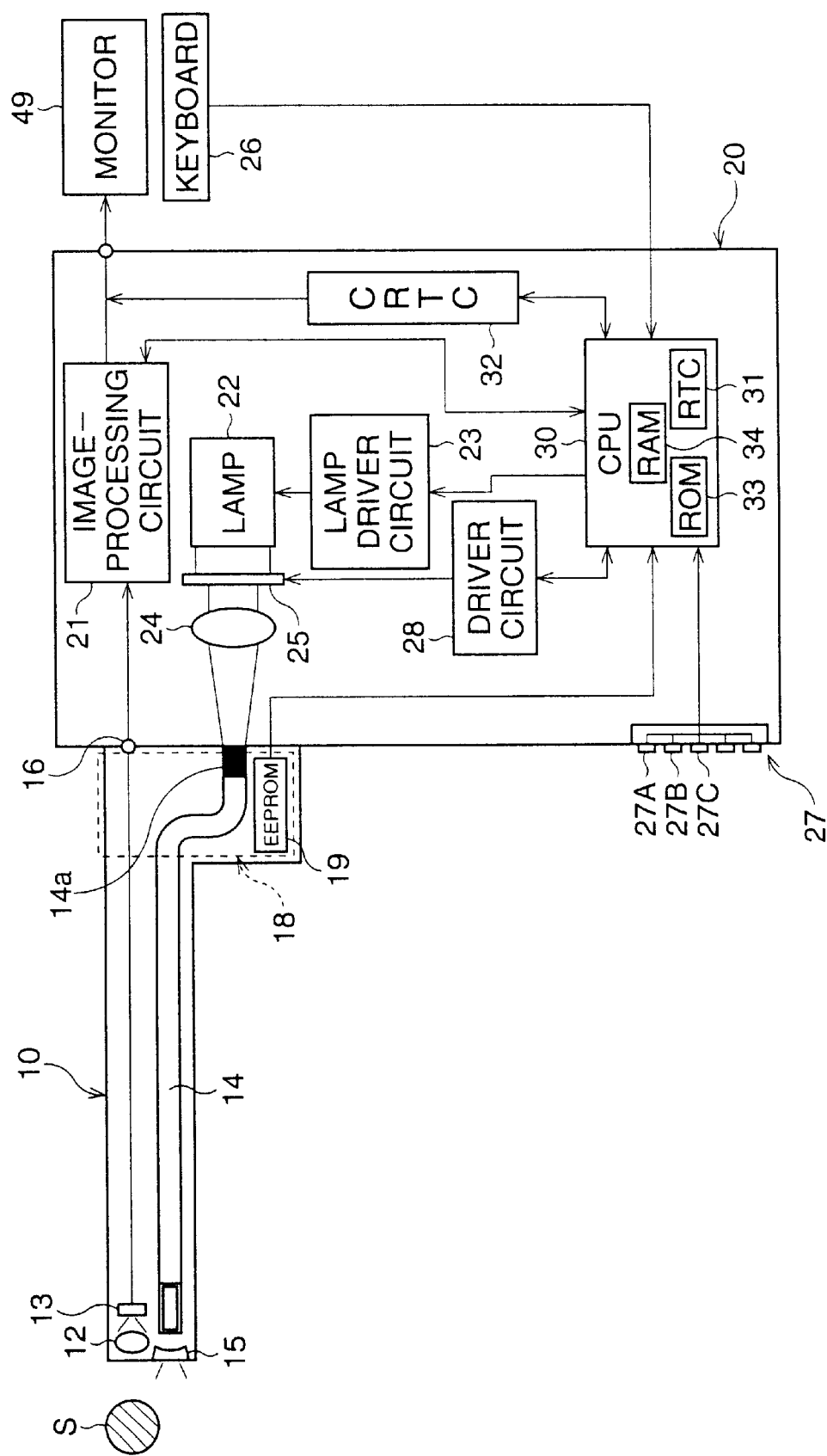
FIG. 1 is a block diagram showing an electronic endoscope of an embodiment of the present invention.

FIG. 1 is a block diagram of an electronic endoscope of the embodiment. This endoscope is used when an operation, an inspection or a treatment regarding an organ, such as a stomach, is performed.

The electronic endoscope includes a video-processor 20 and a video-scope 10. The video-scope 10 is a flexible conduit, and is detachably connected to the video-processor 20. A monitor 49 is also connected to the video-processor 20. During an operation, a proximal end 18 of the video-scope 10 is connected to the video-processor 20, and a distal end of the video-scope 10 is inserted into the body-cavity. When the video-scope 10 is connected to the video-processor 20, data associated with a type of video-scope 10 is read from an EEPROM (Electronic Erasable Programmable ROM) 19 and then fed to a CPU (Central Processing Unit) 30. The electronic endoscope is controlled by the CPU 30.

The video-scope 10 includes a light guide 14 extended therethrough, formed as a bundle of optical fibers. When the proximal end 18 of the video-scope 10 is connected to the video-processor 20, an incidence end 14a of the light guide 14 is optically connected to a lamp 22, such as a halogen lamp, controlled by a lamp driver circuit 23. Thus, light emitted from the lamp 22, is directed to the incidence end 14a of the light guide 14 via a condenser lens 24, and then radiates from the distal end of the light guide 14 toward an object S via a diffusion lens 15.

A stop (diaphragm) 25 is provided between the lamp 22 and the incidence end 14a of the light guide 14, and is driven by a stepping motor (not shown), which rotates by a driving-signal output from a driver circuit 28. The stop 25 is used for adjusting a quantity of light directed from the lamp 22 to the incidence end 14a of the light guide 14. Namely, the stop 25 is used for adjusting a quantity of the illuminating-light radiating from the distal end of the light guide 14.

A CCD (Charge-Coupled-Device) 13, which is an image sensor, is provided at the distal end of the video-scope 10. When an object S is illuminated by the illuminating-light, light reflected from the object S is focused on the CCD 13 via an optical lens 12, so that the object image is formed on the CCD 13.

Photoelectric conversion devices (not shown) are provided on the CCD 13, and red (R), green (G), and blue (B) color mosaic-filter elements are provided in front of the photoelectric conversion devices. Namely, in this embodiment, one chip color method is applied. The object image, formed on the CCD 13, is converted into electrical image-pixel signals corresponding to predetermined colors by the photoelectric conversion devices. These analog image-pixel signals, corresponding to a frame, are successively read from the CCD 13 to an image-processing circuit 21 via a connector 16, i.e., the object image is scanned. In this embodiment, a NTSC color method is applied as a color-television video-standard. Therefore, one frame worth of the analog image-pixel signals is scanned at regular time-intervals of 1/30 sec. However, other color-television methods may be used in alternative embodiments.

In the image-processing circuit 21, one frame worth of the analog image-pixel signals, output from the CCD 13 in order, is separated into analog image-pixel signals corresponding to the red R, analog image-pixel signals corresponding to green G, and analog image-pixel signals corresponding to blue B, respectively. Then, the analog image-pixel signals, corresponding to each color (R, G, B), are amplified and converted into digital image-pixel signals, respectively. Further, the digital image-pixel signals are subjected to various image-processes, such as a reset noise removal and gamma-correction, etc. One frame of luminance signals are successively generated on the basis of the digital image-pixel signals, and then fed to the CPU 30. The stop 25 is controlled by the CPU 30 on the basis of the luminance signals.

The digital image-pixel signals are converted into analog image-pixel signals again in the image-processing circuit 21, and are further converted into the video signals, in short, NTSC signals. The video signals are output from the image-processing circuit 21 to the monitor 49.

Character-code is fed from the CPU 30 to a CRTC (Cathode Ray Tube Controller) 32 to display character information, such as patient's name, age etc, on the monitor 49. In the CRTC 32, character signals corresponding to the character information displayed on the monitor 49 are generated, and the character signals are output from the CRTC 32. Similar to the character information, pointer signals corresponding to a pointer, which is an indicator-mark for pointing to a specific portion in the object image displayed on the monitor 49 (for example, a diseased portion), is generated in the CRTC 32.

The character signals and the pointer signals are superimposed on the video signal output from the image-processing circuit 21, and then the video signal including the character signals and the pointer signals is fed to the monitor 49. One frame worth of the video signals are successively output to the monitor 49 at regular time-intervals of 1/30 sec, thus the object image is displayed on the monitor 49, as a moving picture.

Timing-control signals corresponding to an output-timing of the character and pointer signals output from the CRTC 32 are fed from the CPU 30 to the CRTC 32, thus the character information and the pointer are displayed at a predetermined position on the monitor 49, respectively. A timing generator (not shown), for synchronizing the image-pixel signals read from the CCD 13, the video signals output from the image-processing circuit 21 and the character and pointer signals output from the CRTC 32, is provided in the video-processor 20. Thus, clock pulse signals are fed from the timing generator to the CCD 13, the image-processing circuit 21 and the CRTC 32 by a clock frequency.

A panel switch 27 includes an up-switch 27A, a down-switch 27B and an auto/manual switch 27C. When the up-switch 27A and/or the down-switch 27B are operated by an operator to set a level of brightness of the object image displayed on the monitor 49, operation-signals are input to the CPU 30, and thus the brightness of the object image is adjusted. The auto/manual switch 27C is operated by an operator for selecting a method of an adjustment of the brightness.

When a keyboard 26 is operated, an operation-signal, regarding the object image and the character information and so on, is input to the CPU 30. In this embodiment, an image-area, which is a displaying-area of the object image displayed on the monitor 49, can be enlarged by operating the keyboard 26. In this case, magnifying video signals, corresponding to an enlarged object image on the monitor 49, are obtained by an interpolation processing, which is well known, in the image-processing circuit 21, and are then fed to the monitor 49.

When the object image on the monitor 49 is enlarged, the character and pointer signals are output from the CRTC 32 by a timing corresponding to the enlarged object image, thus the character information and the pointer are displayed at a position corresponding to the enlarged object image, respectively.

In the CPU 30, a ROM 33 which is a nonvolatile memory 33, a RAM 34 which is a volatile memory, and a RTC (Real Time Clock) 31 are provided. In the ROM 33, a reference table, representing display-positions of the character information and the pointer, is stored as data. In the RAM 34, a part of the display-positions of the character information and the pointer, which is read from the reference table, is temporarily stored. Then, the display-positions of the character information and the pointer on the monitor 49 are determined on the basis of the display-positions stored in the ROM 33 and the RAM 34. Further, a list of patients who have been examined using the electronic endoscope is also stored in the RAM 34 as data. A current time and date are read from the RTC 31, and the character-code corresponding to the current date and time is fed to the CRTC 32. Thus, the time and date are displayed on the monitor 49.

Figure 2:
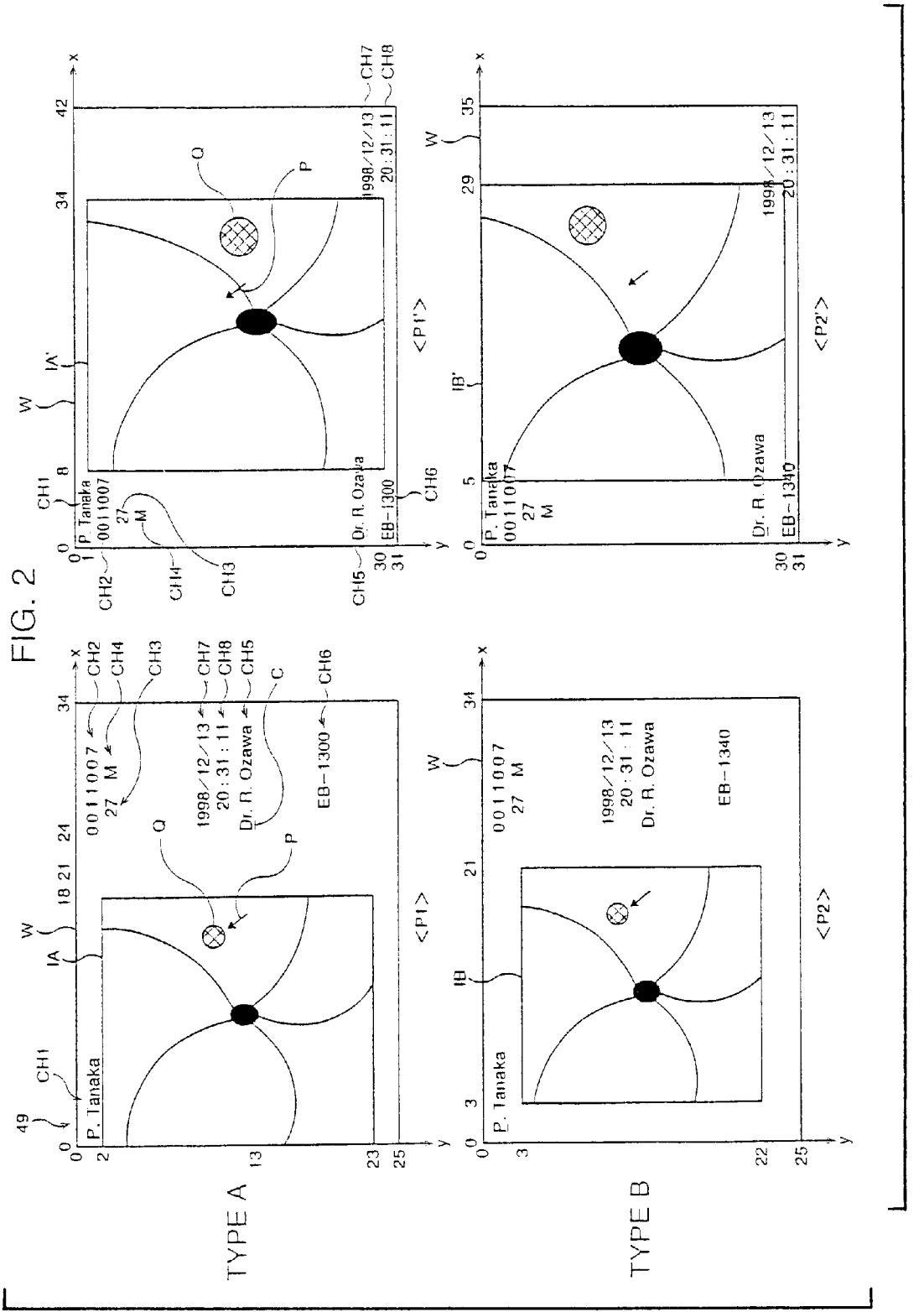
FIG. 2 is a view showing images displayed on a screen of a monitor.
Figure 3:
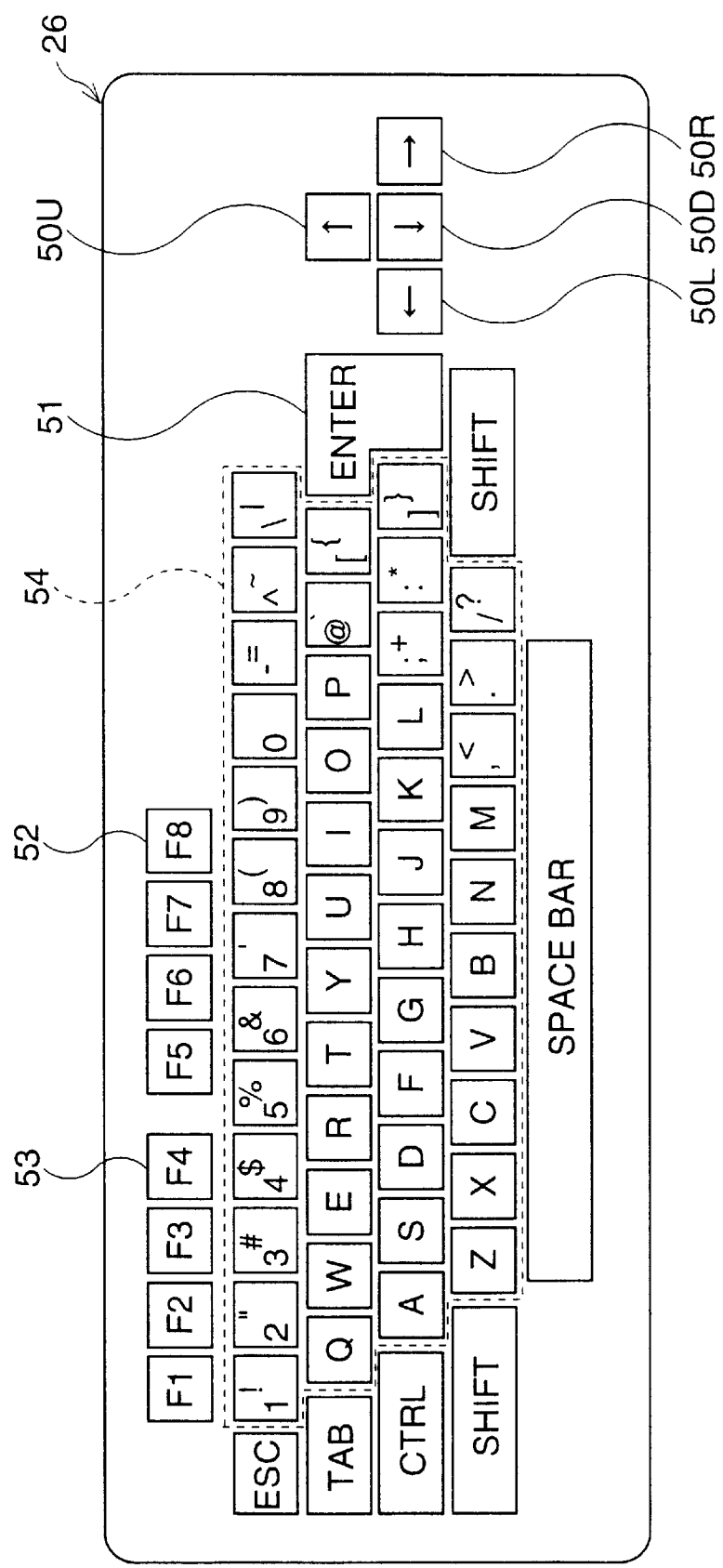
FIG. 3 is a view showing a keyboard.

FIGS. 2 to 4 are views of display-positions of the character information and the pointer. FIG. 2 is a view showing pictures displayed on a screen of the monitor 49. FIG. 3 is a view showing the keyboard 26. FIG. 4 is a view showing the reference table.

In this embodiment, two kinds video-scopes, type A of the video-scope 10 and a type B of the video-scope 10 can be connected to the video-processor 20. Further, regarding the image-area of the object image on the screen, a normal-display or a magnification-display can be selected by operating a F8 (function 8) key 52 on the keyboard 26 (See FIG. 3). The image-area of the object image on the screen is changed by operating the F8 key 52.

A picture P1, shown in FIG. 2, indicates a picture displayed on the screen W of the monitor 49 in a case where the type A of the video-scope 10 is connected to the video-processor 20 and the display-state is the normal-display. The body-cavity image is displayed within a normal image-area IA. Then, the character information, namely, a patient's name CH1, an ID number (patient's registration number) CH2, a patient's age CH3, a patient's sex CH4, a doctor's name CH5, a scope-name CH6, which is a code-name of the video-scope 10 connected to the video-processor 20, a date CH7 and a time CH8 are respectively displayed at a position on the screen W with the object image. Further, the pointer P pointing to a diseased-portion Q is displayed in the normal image-area IA. The pointer P is displayed and erased by operating a F4 (function 4) key 53 (See FIG. 3), as described below. A shifting of the pointer P on the screen W is performed by operating an up-shift key 50U, a down-shift key 50D, a right-shift key 50R, and a left-shift key 50L, shown in FIG. 3. During an operation, the display-state is usually set to normal-display. A size of the normal image-area IA depends on a number of the pixels of the CCD 13 in the type A of the video-scope 10.

When a character key 54 on the keyboard 26 (See FIG. 3) is operated, a letter corresponding to a position, at which a cursor C is displayed (herein, "D" in the doctor's name CH5), is replaced to other letter corresponding to the operated character key, as described later. Then, the position of cursor C is shifted to rightward by one letter worth (herein, "r" in the doctor's name CH5). The shifting of the position of the pointer P and the cursor C is performed by operating an Enter key 51, the up-shift key 50U, the down-shift key 50D, the right-shift key 50R, and the left-shift key 50L (See FIG. 3).

When the F8 key 52 is depressed by the operator in a case where the object image is displayed within the normal image-area IA, the display-state is changed to magnification-display, shown in the picture P1' in FIG. 2, as described later. Thus, the size of the normal image-area IA is enlarged to a large-sized magnifying image-area IA', within which the object image is displayed. The magnifying image-area IA' is located at a center portion of the screen W.

In accordance with the size-change of the image-area, character information is displayed at corner portions of the screen W. A position of each item of character information is shifted beyond the magnifying image-area IA' on the screen W, such that the character information overlaps the object image within the magnifying image-area IA' as little as possible. On the other hand, the display-position of the pointer P is not changed when the display-position of the pointer P is within the magnifying image-area IA'.

Inversely, when the F8 key 52 is depressed by the operator in a case where the object image is displayed within the magnifying image-area IA', the display-state is returned to the normal-display. Therefore, the magnifying image-area IA' is again changed to the normal-image-area IA, and the display-positions of the character information are shifted to the original display-positions, respectively. On the other hand, the position of the pointer P is not changed when the display-position of the pointer P is within the normal image-area IA.

However, when the position of the pointer P is beyond the normal image-area IA or the magnifying image-area IA' in a case where the size-change of the image-area is performed, the position of the pointer P is shifted within the normal image-area IA or the magnifying image-area IA', as described later.

When the type B of the video-scope 10 is connected to the video-processor 20 and the display-state is the normal-display, the object image is displayed within a normal image-area IB, as shown in picture P2 on the screen W in FIG. 2. Note that, as shown in FIG. 2, the normal image-area IB is different from the normal image-area IA because of the difference between the CCD 13 in the type A of the video-scope 10 and the CCD 13 in the type B of the video-scope 10.

Similarly to the type A of the video-scope 10, when the F8 key 52 is depressed by the operator in a case where the object image is displayed within the normal image-area IB, the display-state is changed to the magnification-display, as shown in a picture P2' in FIG. 2. Thus, the size of the normal image-area IB is enlarged to a large-sized magnifying image-area IB', within which the object image is displayed. In accordance with the size-change of the image-area, the character information is displayed at corner portions of the screen W. similarly to the type A of the video-scope 10. When the F8 key 52 is depressed by the operator in a case where the object image is displayed within the magnifying image-area IB', the display-state is returned to normal-display.

The reference table T, shown in FIG. 4, represents x-y coordinates of each item of the character information and the pointer P. As shown in FIG. 2, a x-y coordinate system is defined with respect to the screen W of the monitor 49, and an origin of the x-y coordinate system is positioned at the upper left-most corner of the screen W. Note that, values of x-coordinates ascend from a left-position to right-position. On the other hand, values of y-coordinates ascend from an upper-position to a lower-position.

In the reference table T, the character information is arranged by item (the patient's name CH1, the patient's age CH2, . . . , the time CH8), and x-y coordinates (x,y) of 8 items are respectively represented. In this embodiment, x-y coordinates, corresponding to four image-areas, are prepared for each item. Namely, x-y coordinates (x,y) corresponding to the type A of the video-scope 10 and the normal-display, x-y coordinates (x,y) corresponding to the type A of the video-scope 10 and the magnification-display, x-y coordinates (x,y) corresponding to the type B of the video-scope 10 and the normal-display, and x-y coordinates (x,y) corresponding to the type B of the video-scope 10 and the magnification-display are represented in the reference table T. Note that, the x-y coordinates (x,y) indicate a position of a head letter in each item. For example, when the type A of the video-scope 10 is connected to the video-processor 20 and the display-state is the normal-display, the x-y coordinates of the patient's name CH1 is "(1,1)", which is a position of a letter "P", as shown in FIG. 2.

The reference table T is stored in the ROM 33 (shown in FIG. 1) as data in advance. Namely, x-y coordinates-data is stored in addresses of the ROM 33. Herein, the x-y coordinates (x,y) are represented by using a 10-columns 8-rows array h as given by following formula:

$$(x,y)=(h[cp,vs], h[cp,vs]) \quad (1)$$

Note that, an item variable cp corresponds to the items. For example, the patient's age CH3 corresponds to the item variable cp of "3". On the other hand, a display-position variable vs corresponds to a x-coordinate or a y-coordinate corresponding to the four image-areas. For example, when the type B of the video-scope 10 is connected to the video-processor 20 and the display-state is the normal-display, the display-position variable vs of the x-coordinate is "3", and the display-position variable vs of the y-coordinate is "4".

The array h is utilized in the source code (programming language), and corresponds to the address in the ROM 33. Namely, the x-y coordinates (x,y) are stored in the array h in the source code. When the type B of the video-scope 10 is connected to the video-processor 20 and the display-state is the normal-display, the x-y coordinates (x,y) of the doctor's name CHS is:

$$(x,y)=(h[5,5],h[5,6])=(24,13) \quad (2)$$

Further, in this embodiment, when the type of the video-scope 10 and the display-state are determined, as described later, corresponding x-y coordinates-data is read from the ROM 33 and then temporarily stored in the RAM 34 (shown in FIG. 1). Herein, the x-y coordinates (x,y) stored in the RAM 34 are represented by using a 10-columns 2-rows array H, corresponding to addresses in the RAM 34, as follows:

$$(x,y)=(H[cp,1], H[cp,2]) \quad (3)$$

For example, when the type B of the video-scope 10 is connected to the video-processor 20 and the display-state is the magnification-display, the x-y coordinates (x,y) of the item variable cp of "5" (doctor's name CHS) are:

$$(x,y)=(H[5,1],H[5,2])=(0,28) \quad (4)$$

Note that, the array H[cp,1] indicates the x-coordinate of the item corresponding to the item variable cp, and the array H[cp,2] indicates the y-coordinate of the item corresponding to the item variable cp.

While the display-state is not changed or the exchange of the video-scope 10 is not performed, the character information is displayed on the screen in accordance with the x-y coordinates stored in the array H. When the display-state is changed or the exchange of the video-scope 10 is performed, as described later, corresponding x-y coordinates-data is read from the array h and stored in the array H. Thus, the x-y coordinates (x,y) in the array H are rewritten. Then, the character information is displayed on the basis of the x-y coordinates (x,y) newly stored in the array H.

In the reference table T, a minimum limitation-position of the pointer $A_{min}$ corresponding to the item variable "9" and a maximum limitation-position of the pointer $A_{max}$. corresponding to the item variable "10" are also represented. As shown in FIGS. 2 and 4, x-y coordinates (x,y) of the minimum and maximum limitation-position of the pointer $A_{min}$ and $A_{max}$ indicate corner-positions of one of the image-areas IA, IA', IB, IB'. Note that, the x-y coordinates (x,y) of the minimum and maximum limitation-position of the pointer $A_{min}$ and $A_{max}$ respectively represent a head position of the pointer of an arrow.

As mentioned above, the pointer P should be displayed within the image-area of the object image. Therefore, when the display-state is changed or the exchange of the video-scope 10 is performed, the display-position of the pointer P is determined depending upon the maximum limitation-position of the pointer $A_{max}$ and the minimum limitation-position of the pointer $A_{min}$, such that the display-position of the pointer P is not beyond the image-area of the object image. In this embodiment, the pointer P is shifted to a boundary of the image-area when the display-position of the pointer P is beyond the image-area by the size-change of the image-area, as described later. The x-y coordinates (x,y) regarding above the display-positions of the pointer P is also stored in the array h and further the array H.

In this way, the display-positions of the character information and the pointer P are determined depending upon the reference table T.

Note that, as shown in FIG. 2, when the display-state is magnification-display, a number of letters, which can be displayed in each column on the screen W, of the type A of the video-scope 10 is different from that of the type B of the video-scope 10 (See Pictures P1' and P2') Here, the number of letters of the type A of the video-scope 10 is "42", while, the number of letters of the type B of the video-scope 10 is "35". This difference is because the number of pixels of the CCD 13 provided in the type A of the video-scope 10 is different from that of the CCD 13 provided in the type B of the video-scope 10, as is conventionally well known. Namely, The clock frequency, output from the timing generator (not shown in FIG. 1) to the CCD 13, differs in accordance with the number of the pixels of the CCD 13, i.e., the type of the video-scope 10 when the display-state is the magnification-display. Therefore, for example, as shown in FIG. 4, the x-y coordinates "(35,29)" of the date CH7 in the type A of the video-scope 10 is different from the x-y coordinates "(26,30)" of the date CH7 in the type B of the video-scope 10, though the display-position of the date CH7 in the type A of the video-scope 10 and the display-position of the date CH 7 in the type B of the video-scope 10 are substantially the same on the screen W, as shown in the pictures P1' and P2' of FIG. 2.

Figure 5:
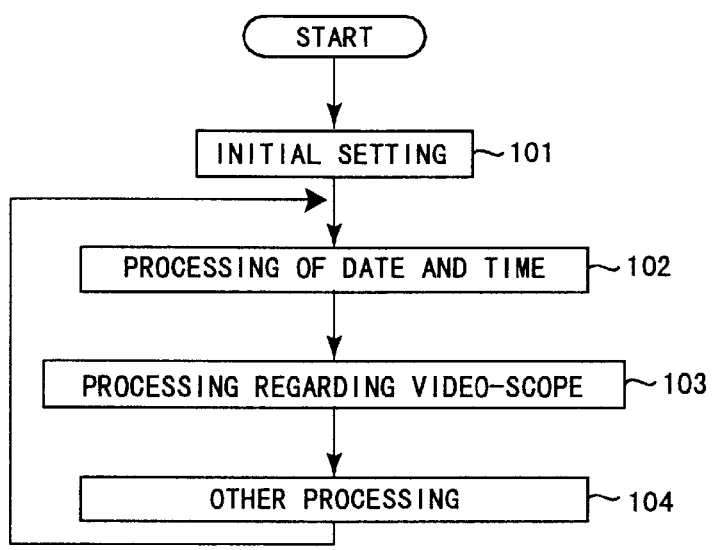
FIG. 5 is a view showing a main routine regarding operations of the electronic endoscope as a whole.

FIG. 5 is a view showing a main routine regarding operations of the electronic endoscope as a whole. When electric power is turned ON, the main routine is started.

In Step 101, the x-y coordinates (x,y) stored in the array H, the stop 25 and so on, are subjected to an initial setting, respectively.

In Step 102, a processing regarding a displaying of the time and the date is performed. In Step 103, a processing regarding the video-scope 10 is performed. In Step 104, other processing, for example, a level of the brightness of the light source 19 is adjusted in accordance with the operation of the panel switches 27.

These operations of the electronic endoscope are executed until the electric power is turned OFF. In Steps 102 to 104, subroutines, as described later, are respectively performed.

Figure 6:
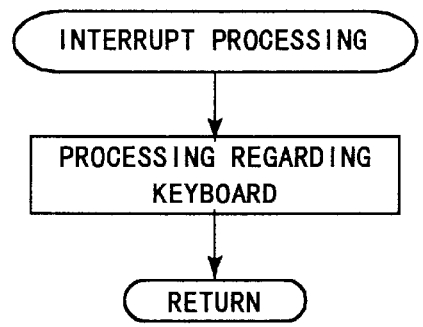
FIG. 6 is a view showing an interrupt routine regarding an operation of the keyboard.

FIG. 6 is a view showing an interrupt routine regarding the operation of the keyboard 26, as described later. This interrupt processing interrupts the operations of the electronic endoscope shown in FIG. 5.

Figure 7:
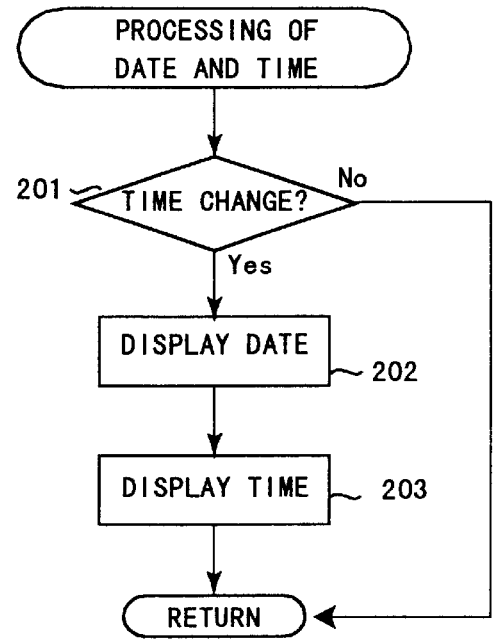
FIG. 7 is a view showing a subroutine of Step 102 in FIG. 5.

FIG. 7 is a subroutine of Step 102 in FIG. 5.

In Step 201, it is determined whether or not data regarding the time and the date, read from the RTC 31, has changed compared to a preceding date and time, read at a preceding processing. Namely, it is determined whether or not one second has passed compared to the preceding processing. When the time has passed by more than one second, the process goes to Step 202. On the other hand, when the time has not passed by more than one second, this subroutine is terminated.

In Step 202, the date (a year, a month, a day) CH7 is displayed on the screen W on the basis of the x-y coordinates (x,y) stored in the array H. For example, when the type A of the video-scope 10 is connected to the video-processor 20 and the display-state is the normal-display, the date CH7 is displayed such that a head numeral "1" in the date CH7 is located at (24,9), as shown in FIG. 2. Note that, the x-coordinate "24"and the y-coordinate "9" is respectively stored in the array H[7,1] and the array H[7,2].

In Step 203, the real time (hour, minute, second) CH8 is displayed on the screen W on the basis of the x-y coordinates (x,y) stored in the array H, similarly to the date CH8. After the time and the date are displayed at the determined position, this subroutine is terminated, and the process then returns to Step 102 of FIG. 5.

Figure 8:
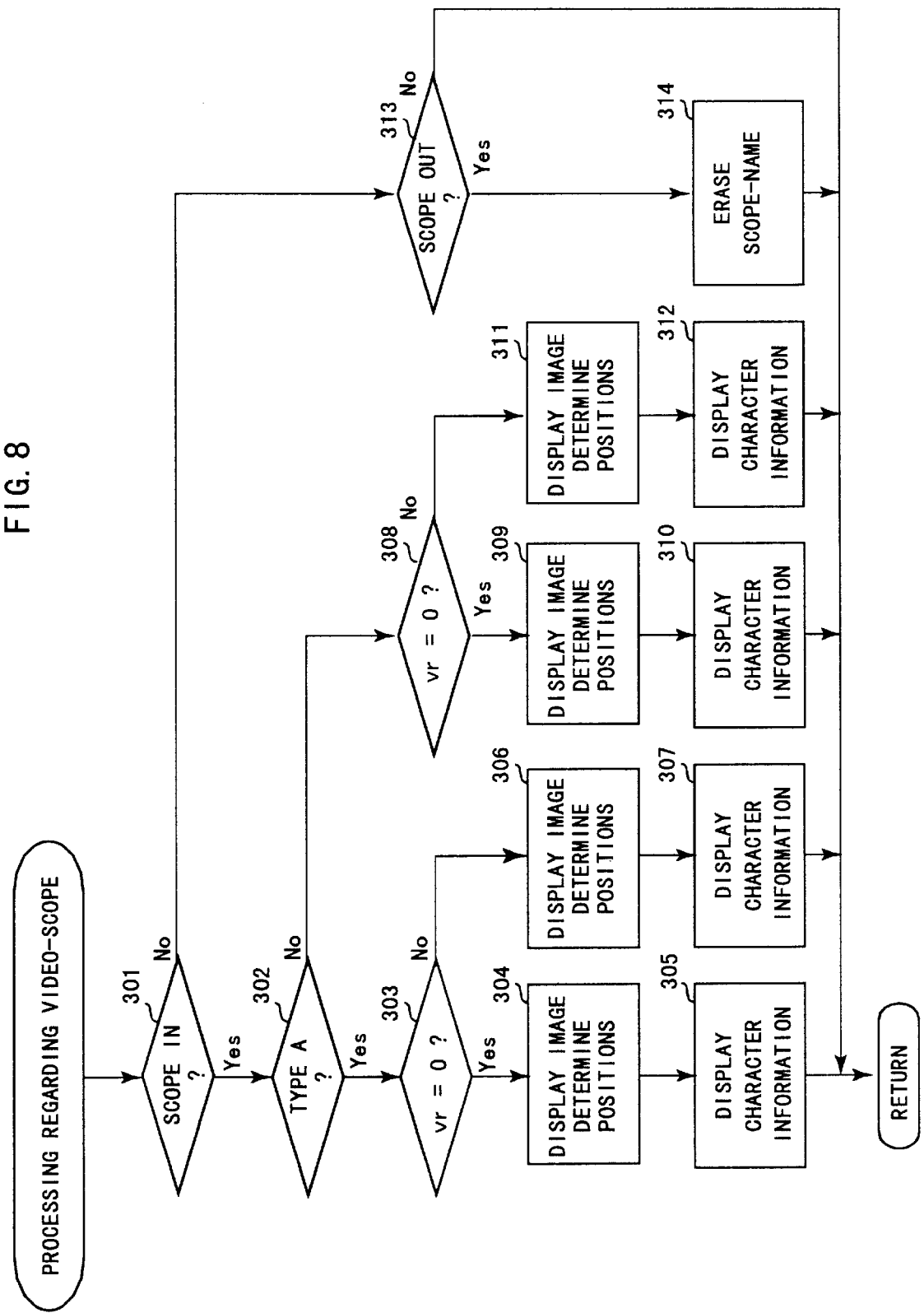
FIG. 8 is a view showing a subroutine of Step 103 in FIG. 5.

FIG. 8 is a view showing a subroutine of Step 103 in FIG. 5.

In Step 301, it is determined whether or not the video-scope 10 is newly connected to the video-processor 20. When it is determined that the video-scope 10 is newly connected to the video-processor 20, namely, the exchange of the video-scope 10 has been performed, the process goes to Step 302.

In Step 302, it is determined whether the video-scope 10, which has been newly connected to the video-processor 20, is the type A of the video-scope 10. Note that, this determination is based on the data, read from the EEPROM 19 in the video-scope 10 (shown in FIG. 1). When it is determined that the connected video-scope 10 is the type A, the process goes to Step 303.

In Step 303, it is determined whether or not a display variable vr is 0. Namely, it is determined whether the display-state before the exchange of the video-scope 10 is the normal-display. The display variable vr indicates the normal-display or the magnification-display. When the display variable vr is 1, the display-state is the magnification-display, while, when the display variable vr is 0, the display-state is the normal-display.

When it is determined that the display variable vr is 0 at Step 303, the process goes to Step 304.

In Step 304, the object image is displayed within the image-area IA. Further, the display-positions of the character information are determined from the reference table T. Namely, the x-y coordinates (x,y) stored in the array h[cp,1] and the array h[cp,2], corresponding to the type A of the video-scope 10 and the normal-display, is read, and then temporarily stored in the array H[cp,1] and the array H[cp,2]. Then, the process goes to Step 305.

In Step 305, each item of character information is displayed at the determined position on the basis of the x-y coordinates (x,y) stored in the array H[cp,1] and the array H[cp,2], as shown in the picture P1 displayed on the screen W in FIG. 2. At this time, the scope-name of the type A of video-scope 10.is displayed. After the character information is displayed, this subroutine is terminated, and then the process returns to Step 103 in FIG. 5.

When it is determined that the display variable vr is 1 at Step 303, namely, the display-state is the magnification-display, the process goes to Step 306.

In Step 306, the object image is displayed within the image-area IA'. Further, the display-positions of the character information are determined, similarly to Step 304. Note that, in this case, the x-y coordinates (x,y), stored in the array h[cp,3] and the array h[cp,4], corresponding to the type A of the video-scope 10 and magnification-display, is read and then temporarily stored in the array H[cp,1] and the array H[cp,2]. Then, the process goes to Step 307.

In Step 307, each item of character information is displayed at the determined position on the basis of the x-y coordinates (x,y) stored in the array H[cp,1] and the array H[cp,2], as shown in the picture P1' displayed on the screen W in FIG. 2. After the character information is displayed, this subroutine is terminated, and then the process returns to Step 103 in FIG. 5.

On the other hand, when it is determined that type B of the video-scope 10 is newly connected to the video-processor 20 at Step 302, the process goes to Step 308.

In Step 308, it is determined whether or not the display variable vr is 0. When it is determined that the display variable vr is 0, namely, the display-state is the normal-display, the process goes to Step 309.

In Step 309, the object image is displayed within the image-area IB. Further, the display-positions of the character information are determined from the reference table T. Namely, the x-y coordinates (x,y) stored in the array h[cp,5] and the array h[cp,6], corresponding to the type B of the video-scope 10 and the normal-display, is read, and then temporarily stored in the array H[cp,1] and the array H[cp,2]. Then, the process goes to Step 310.

In Step 310, each item of character information is displayed at the determined position on the basis of the x-y coordinates (x,y) stored in the array H[cp,1] and the array H[cp,2], as shown in the picture P2 displayed on the screen W in FIG. 2. At this time, the scope-name of the type B of video-scope 10 is displayed. After the character information is displayed, this subroutine is terminated, and then the process returns to Step 103 in FIG. 5.

When it is determined that the display variable vr is 1 at Step 308, namely, the display-state is magnification-display, the process goes to Step 311.

In Step 311, the object image is displayed within the image-area IB'. Further, the display-positions of the character information are determined, similarly to Step 309. Note that, in this case, the x-y coordinates (x,y) stored in the array h[cp,7] and the array h[cp,8], corresponding to the type B of the video-scope 10 and magnification-display, is read and then temporary stored in the array H[cp,1] and the array H[cp,2]. Then, the process goes to Step 312.

In Step 312, each of character information is displayed at the determined position on the basis of the x-y coordinates (x,y) stored in the array H[cp,1] and the array H[cp,2]), as shown in the picture P2' displayed on the screen W in FIG. 2. After the character information is displayed, this subroutine is terminated, and then the process returns to Step 103 in FIG. 5.

When it is determined that the video-scope 10 is not newly connected to the video-processor 20 at Step 301, the process goes to Step 313.

In Step 313, it is determined whether the video-scope 10 is detached from the video-processor 20.

When it is determined that the video-scope 10 is detached from the video-processor 20, the process goes to Step 314. In Step 314, the object image and the scope-name of the video-scope 10 are erased from the screen W. At this time, the object image is not displayed on the screen W. Then, this subroutine is terminated and the process returns to Step 103 of FIG. 5.

On the other hand, when it is determined that the video-scope 10 is not detached from the video-processor 20, namely, the video-scope 10 is not changed, the subroutine is terminated and then the process returns to Step 103 of FIG. 5.

As mentioned above, when the exchange of the video-scope 10 is performed, the display-positions of the character information are determined depending upon the corresponding x-y coordinates (x,y) stored in the array h.

Figure 9:
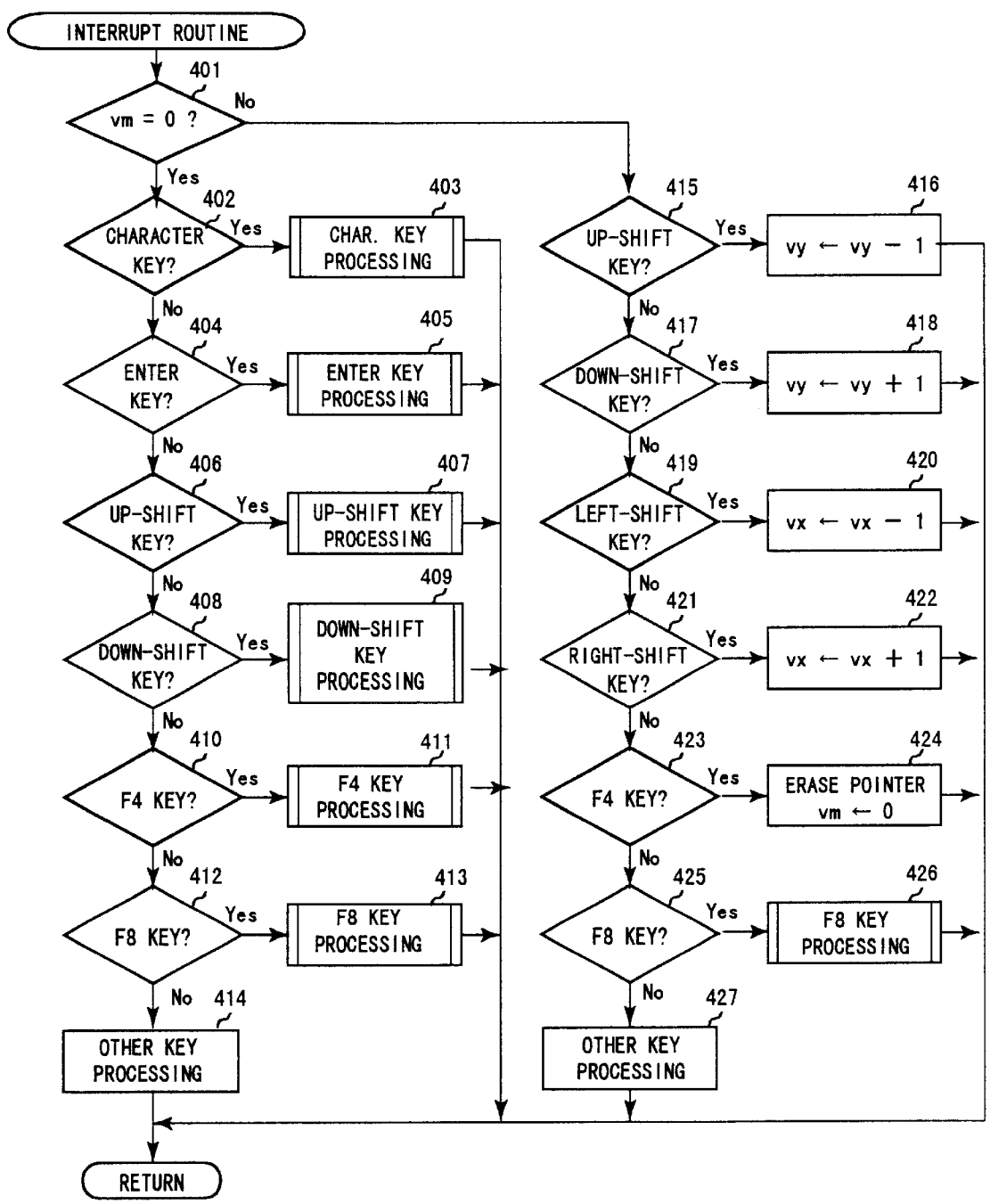
FIG. 9 is a view showing in detail the interrupt routine shown in FIG. 6.

FIG. 9 is a view showing the interrupt routine of FIG. 6 in detail. When any key on the keyboard 26 is operated, this routine is started.

In Step 401, it is determined whether the pointer display variable vm is 0, namely, whether the pointer P is not displayed on the screen W of the monitor 49. Note that, the pointer display variable vm is 1 when the pointer P is displayed, while the pointer display variable vm is 0 when the pointer P is not displayed. When the keyboard 26 is manipulated while the pointer P is displayed on the screen W, Steps 415 to 427 are performed. On the other hand, when the keyboard 26 is manipulated while the pointer P is not displayed on the screen W, Steps 402 to 414 are performed.

When it is determined that the pointer display variable vm is 0 at Step 401, the process goes to Step 402.

In Step 402, it is determined whether or not one of the character keys 54 (shown in FIG. 3) on the keyboard 26 is operated by the operator. When it is determined that one of the character keys 54 is operated, the process goes to Step 403, wherein a processing corresponding to the character keys 54 is performed. Then, this interrupt routine is terminated. On the other hand, when it is determined that none of the character keys 54 are operated at Step 402, the process goes to Step 404.

In Step 404, it is determined whether or not the Enter key 51 (shown in FIG. 3) on the keyboard 26 is operated by the operator. When it is determined that the Enter key 53 is operated, the process goes to Step 405, wherein a processing corresponding to the Enter key 53 is performed. Then, this interrupt routine is terminated. On the other hand, when it is determined that the Enter key 53 is not operated at Step 404, the process goes to Step 406.

In Step 406, it is determined whether or not the up-shift key 50U (shown in FIG. 3) on the keyboard 26 is operated. When it is determined that the up-shift key 50U is operated, the process goes to Step 407, wherein a processing corresponding to the up-shift key 50U is performed. Then, this interrupt routine is terminated. On the other hand, when it is determined that the up-shift key 50U is not operated at Step 406, the process goes to Step 408.

In Step 408, it is determined whether or not the down-shift key 50D (shown in FIG. 3) on the keyboard 26 is operated. When it is determined that the down-shift key 50D is operated, the process goes to Step 409, wherein a processing identical to Step 405 is performed. Then, this routine is terminated. On the other hand, when it is determined that the down-shift key 50D is not operated at Step 408, the process goes to Step 410.

In Step 410, it is determined whether or not the F4 key 53 (shown in FIG. 3) on the keyboard 26 is operated. When it is determined that the F4 key 53 is operated, the process goes to Step 411, wherein a processing corresponding to the F4 key 53 is performed. Then, the interrupt routine is terminated. On the other hand, when it is determined that the F4 key 53 is not operated at Step 410, the process goes to Step 412.

In Step 412, it is determined whether or not the F8 key 52 (shown in FIG. 3) on the keyboard 26 is operated. When it is determined that the F8 key 52 is operated, the process goes to Step 413, wherein a processing corresponding to the F8 key 52 is performed. Then, the interrupt routine is terminated. On the other hand, when it is determined that the F8 key 52 is not operated at Step 412, the process goes to Step 414.

In Step 414, a processing regarding other keys (for example, ESC key) on the keyboard 26 is performed. Then, this interrupt routine is finished.

When it is determined that the pointer display variable vm is 1 at Step 401, namely, the pointer P is displayed on the screen W, the process goes to Step 415.

In Step 415, it is determined whether or not the up-shift key 50U on the keyboard 26 is operated. When it is determined that the up-shift key 50U is operated, the process goes to Step 416.

In Step 416, the pointer P is shifted upward along a y-direction by one coordinate worth only when a following formula (5) is satisfied regarding the display-position of the pointer P.

$$vy > H[9,2] \quad (5)$$

Note that, a value of the y-coordinate of the pointer P is denoted by "vy", and the y-coordinate of the minimum limitation-position of the pointer $A_{min}$ is stored in the array H[9,2]). For example, when the type A of the video-scope 10 is connected to the video-processor 20 and the display-state is the normal-display, as shown in FIG. 4, the formula (6), which corresponds to the formula (5), is:

$$vy > 2 \quad (6)$$

When the formula (5) is satisfied, the pointer P is shifted upward by one coordinate worth. In other words, the value of the y-coordinate vy is decremented by 1. For example, the pointer P, the y-coordinate of which is "20", is shifted to the position of y-coordinate "19". If the formula (5) is not satisfied, the pointer P is not shifted such that the display-position of the pointer P remains within the image-area. After Step 416 is executed, the interrupt routine is terminated.

On the other hand, when it is determined that the up-shift key 50U is not operated at Step 415, the process goes to Step 417.

In Step 417, it is determined whether or not the down-shift key 50D in the keyboard 26 is operated. When it is determined that the down-shift key 50D is operated, the process goes to Step 418.

In Step 418, the pointer P is shifted downward along the y-direction by one coordinate worth only when a following formula (7) is satisfied regarding the display-position of the pointer P.

$$vy < H[10,2] \quad (7)$$

The y-coordinate of the maximum limitation-position of the pointer $A_{max}$ is stored in the array H[10,2]. For example, when the type A of the video-scope 10 is connected to the video-processor 20 and the display-state is the normal-display, formula (8), which corresponds to the formula (7), is:

$$vy < 23 \quad (8)$$

When the formula (7) is satisfied, the pointer P is shifted downward by one coordinate worth. In other words, the value of the y-coordinate vy is incremented by 1. For example, the pointer P, the y-coordinate of which is "20", is shifted to the position of the y-coordinate "21". If the formula (7) is not satisfied, the pointer P is not shifted. After Step 418 is executed, the interrupt routine is terminated.

On the other hand, when it is determined that the down-shift key 50D is not operated at Step 417, the process goes to Step 419.

In Step 419, it is determined whether or not the left-shift key 50L in the keyboard 26 is operated. When it is determined that the left-shift key 50L is operated, the process goes to Step 420.

In Step 420, the pointer P is shifted leftward along a x-direction by one coordinate worth, only when a following formula (9) is satisfied regarding the display-position of the pointer P.

$$vx > H[9,1] \quad (9)$$

A value of the x-coordinate of the pointer P is denoted by "vx", and the x-coordinate of the minimum limitation-position of the pointer $A_{min}$ is stored in the array H[9,1]. For example, when the type A of the video-scope 10 is connected to the video-processor 20 and the display-state is the normal-display, as shown in FIG. 4, formula (10), which corresponds to the formula (9), is:

$$vx > 0 \quad (10)$$

When the formula (9) is satisfied, the pointer P is shifted leftward by one coordinate worth. In other words, the value of the x-coordinate "vx" is decremented by 1. For example, the pointer P, the x-coordinate of which is "17", is shifted to the position of x-coordinate "16". If the formula (9) is not satisfied, the pointer P is not shifted. After Step 420 is executed, the interrupt routine is terminated.

On the other hand, when it is determined that the left-shift key 50L is not operated at Step 419, the process goes to Step 421.

In Step 421, it is determined whether or not the right-shift key 50R in the keyboard 26 is operated. When it is determined that the right-shift key 50R is operated, the process goes to Step 422.

In Step 422, the pointer P is shifted rightward along the x-direction by one coordinate worth only when a following formula (11) is satisfied regarding the display-position of the pointer P.

$$vx < H[10,1] \quad (11)$$

The x-coordinate of the minimum-limitation-position of the pointer $A_{max}$ is stored in the array H[10,1]. For example, when the type A of the video-scope 10 is connected to the video-processor 20 and the display-state is the normal-display, formula (12), corresponds to the formula (11), is:

$$vx < 18 \quad (12)$$

When the formula (11) is satisfied, the pointer P is shifted rightward by one coordinate worth. In other words, the value of the x-coordinate vx is incremented by 1. For example, the pointer P, the x-coordinate of which is "15", is shifted to the position of the x-coordinate "16". If the formula (11) is not satisfied, the pointer P is not shifted. After Step 422 is executed, the interrupt routine is terminated.

On the other hand, when it is determined that the right-shift key 5OR is not operated at Step 421, the process goes to Step 423.

In Step 423, it is determined whether or not the F4 key 53 on the keyboard 26 is operated. When it is determined that the F4 key 53 is operated, the process goes to Step 424, wherein the pointer P is erased from the screen W of the monitor 49, and further the pointer display variable vm is set to 0. Then, the interrupt routine is terminated. On the other hand, when it is determined that the F4 key 53 is not operated at Step 423, the process goes to Step 425.

In Step 425, it is determined whether or not the F8 key 52 on the keyboard 26 is operated. When it is determined that the F8 key 52 is operated, the process goes to Step 426, wherein a processing corresponding to the F8 key 52 is performed. Then, the interrupt routine is terminated. On the other hand, when it is determined that the F8 key 52 is not operated at Step 425, the process goes to Step 427. In Step 427, the process equal to Step 414 is performed, and then the interrupt routine is terminated. Note that, in Step 426, as described later, the display-position of the pointer P is adjusted.

As mentioned above, the process for operating the keyboard 26 is performed at Steps 401 to 427. Then, as described later, subroutines are performed at Steps 403, 405, 407, 409, 411, 413, 426, respectively.

Figure 10:
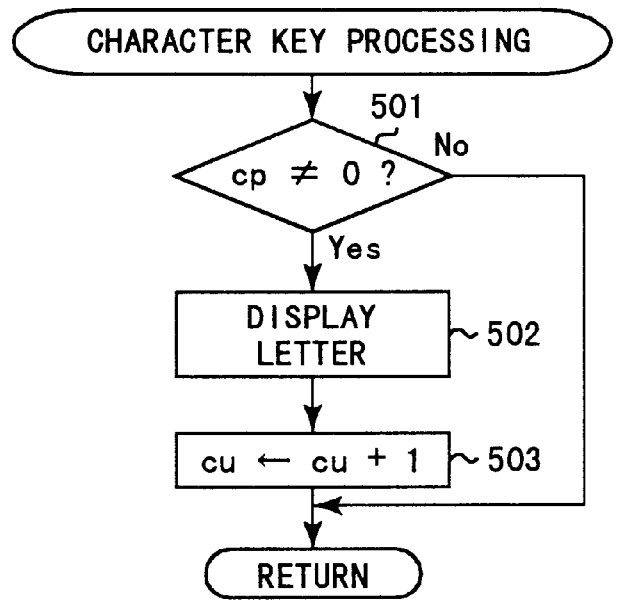
FIG. 10 is a view showing a subroutine of Step 403 in FIG. 9.

FIG. 10 is a subroutine of Step 403 in FIG. 9. This subroutine is performed when one of the character keys 54 is depressed.

In Step 501, it is determined whether the item variable cp is 0, namely, whether the cursor C is not displayed on the monitor 46. The item variables 1 to 6 correspond to the patient's name CH1 through to the scope-name CH6 of the character information respectively. When the item variable cp is 0, the cursor C is not displayed.

When it is determined that the item variable cp is not 0, the process goes to Step 502.

In Step 502, a letter corresponding to the depressed character key among the character keys 54 is input at a position corresponding to the display-position of the cursor C. Then, at Step 503, a cursor position variable cu is incremented by 1, thus the cursor C is shifted rightward by one letter worth Note that, the cursor position variable cu corresponds to a cursor's display-position in each item of the character information. Further note that, the cursor C is located at the head letter in each of the character information when the cursor position variable cu is 0, as shown in the picture P1 of FIG. 2. After the letter is input and the cursor C is shifted, the subroutine is terminated and then the process returns to Step 403 in FIG. 9.

In this way, the character information is rewritten by operating the character keys 54.

On the other hand, when it is determined that the item variable cp is 0 at Step 501, this subroutine is terminated and the process returns to Step 403 in FIG. 9.

Figure 11:
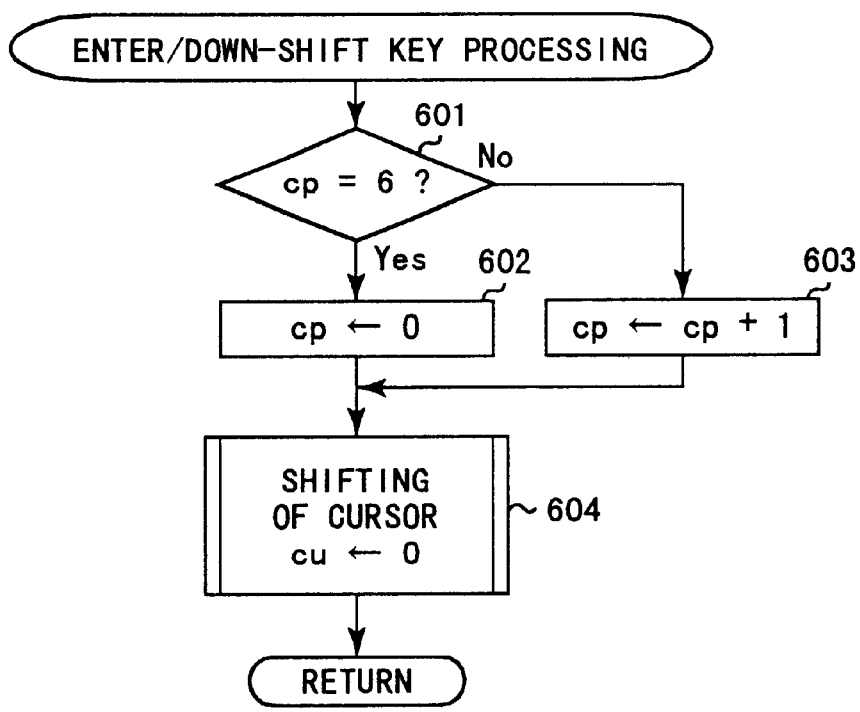
FIG. 11 is a view of a subroutine of Steps 405 and 409 in FIG. 9.

FIG. 11 is a 'subroutine of Steps 405 and 409 in FIG. 9. As described above, this subroutine is performed when the Enter key 51 or the up-shift key 50U is depressed.

In Step 601, it is determined whether the item variable cp is 6, namely, whether the cursor C is located at the scope-name of the video-scope CH6 on the screen W. When it is determined that the item variable cp is 6, the process goes to Step 602, wherein the item variable cp is set to 0. Then the process goes to Step 604.

On the other hand, when it is determined that the item variable cp is not 6 at Step 601, the process goes to Step 603, wherein the item variable cp is incremented by 1. For example, when the item variable cp is 5 corresponding to the doctor's name CH5, the item variable cp is set to 6, corresponding to the scope-name CH6. Then, the process goes to Step 604.

In Step 604, the cursor C is shifted to a position of the item corresponding to the item variable cp, which is set to at Step 602 or Step 603, and further the cursor position variable cu is set to 0. Namely, the cursor C is shifted to the head letter in the item corresponding to the item variable cp, which is set at Step 602 or 603.

Figure 12:
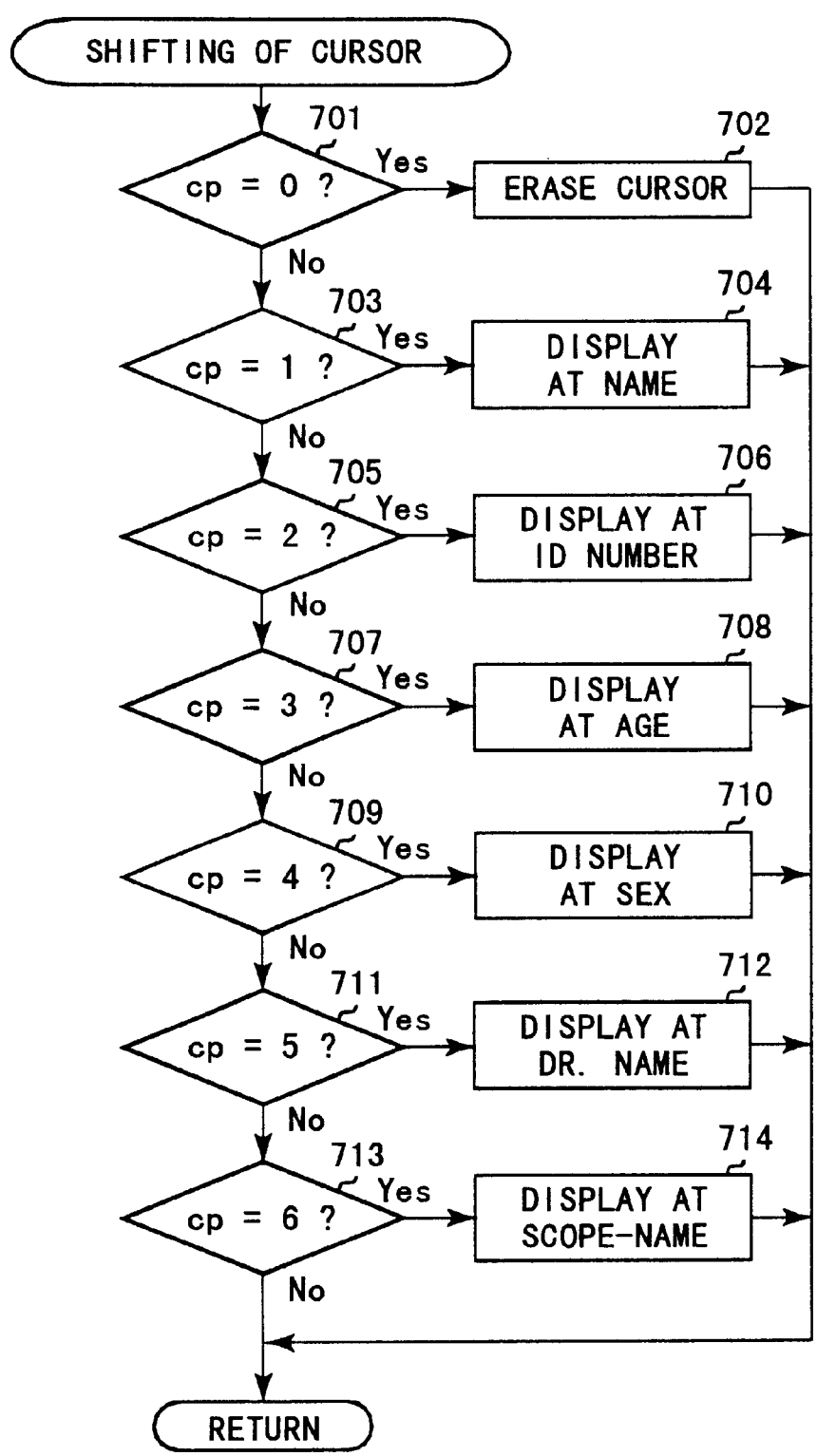
FIG. 12 is a view showing a subroutine of Step 604 in FIG. 11.

FIG. 12 is a subroutine of Step 604 in FIG. 11.

In Step 701, it is determined whether or not the item variable cp is 0, namely, whether the item variable cp is set to 0 at Step 602 in FIG. 11. When it is determined that the item variable cp is 0, the process goes to Step 702, wherein the cursor C is erased from the screen W of the monitor 46. Then, this subroutine is terminated. On the other hand, when it is determined that the item variable cp is not 0, the process goes to Step 703.

In Step 703, it is determined whether or not the item variable cp is 1, namely, whether the item variable cp is set to 1 at Step 603 in FIG. 11. When it is determined that the item variable cp is 1, the process goes to Step 704, wherein the cursor C is displayed at the position corresponding to the head letter in the patent's name CH1. Note that, the x-y coordinates (x,y) of the head letter position is stored in the array H. For example, when the type B of the video-scope 10 is connected to the video-processor 20 and the display-state is the normal-display, as shown in the picture P2 of FIG. 2, the x-y coordinates (x,y) of the position of the cursor C is:

$$(x,y)=(H[1,1], H[1,2])=(1,1) \qquad (13)$$

After Step 704 is performed, this subroutine is terminated.

On the other hand, when it is determined that the item variable cp is not 1 at Step 703, the process goes to Step 705.

In Steps 705 to 714, the value of the item variable cp is determined, similarly to Step 703, and then the cursor C is displayed depending upon the item variable cp, similarly to Step 704. Note that, the display-position of the cursor C is in accordance with the x-y coordinates (x,y) stored in the array H as following:

$$(x,y)=(H[cp,1],H[cp,2]) \qquad (14)$$

For example, when it is determined that the item variable cp is 3 at Step 707 in a case where the type A of the video-scope 10 is connected to the video-processor 20 and the display-state is the normal-display, as shown in the picture P1 of FIG. 2, the cursor C is displayed at following display-position at Step 708:

$$(X,y)=(H[3,1],H[3,2])=(24,2) \qquad (15)$$

In this way, the cursor C is shifted to the head letter in the next item when the Enter key 51 or the down-shift key 50D is depressed. For example, when the Enter key 51 is depressed in a case where the cursor C is located at the doctor's name CH5, the cursor C is shifted to the head letter in the scope-name CH6. At this time, the display-position of the cursor C is determined in accordance with the x-y coordinates (x,y) stored in the array H. After the cursor C is displayed at the determined position, this subroutine is terminated, and the process returns to Step 604 in FIG. 10.

Figure 13:
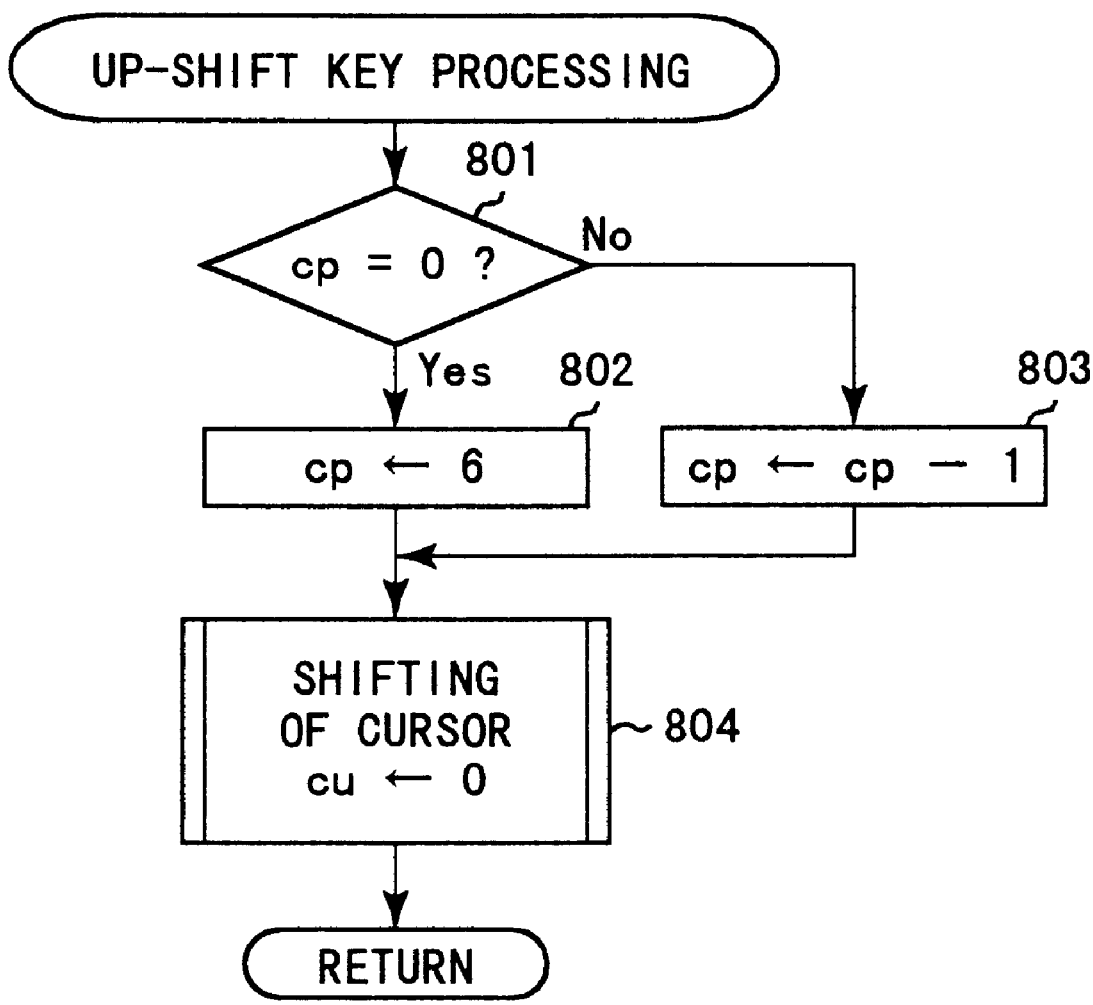
FIG. 13 is a view showing a subroutine of Step 407 in FIG. 9.

FIG. 13 is a subroutine of Step 407 in FIG. 9. As described above, this subroutine is performed when the up-shift key 50U is depressed.

In Step 801, it is determined whether or not the item variable cp is 0, namely, whether the cursor C is not displayed on the screen W. When it is determined that the item variable cp is 0, the process goes to Step 802, wherein the item variable cp is set to 6. Then, the process proceeds to Step 804.

On the other hand, when it is determined that the item variable cp is not 0, the process goes to Step 803, wherein the item variable cp is decremented by 1. For example, when the item variable cp is 5 corresponding to the doctor's name CH5, the item variable cp is set to 4, corresponding to the patient's sex CH4. Then, the process proceeds to Step 804.

In Step 804, the cursor C is shifted to the item corresponding to the item variable cp, which is set at Step 802 or 803. Then, the cursor position variable cu is set to 0. Namely, the cursor C is displayed at a position corresponding to the head letter in the character information. Note that, Steps 701 to 714 shown in FIG. 11 is performed at Step 804, similarly to Step 604 in FIG. 12. After the cursor C is shifted, this subroutine is terminated and then the process returns to Step 407 in FIG. 9.

In this way, the cursor C is shifted to the head letter in the next item when the up-shift key SOU is depressed, similarly to the Enter key 51 or the down-shift key 50D. Note, the shifting-direction of the up-shift key 50U is opposite to the shifting-direction of the Enter key 51 or the down-shift key SOD.

Figure 14:
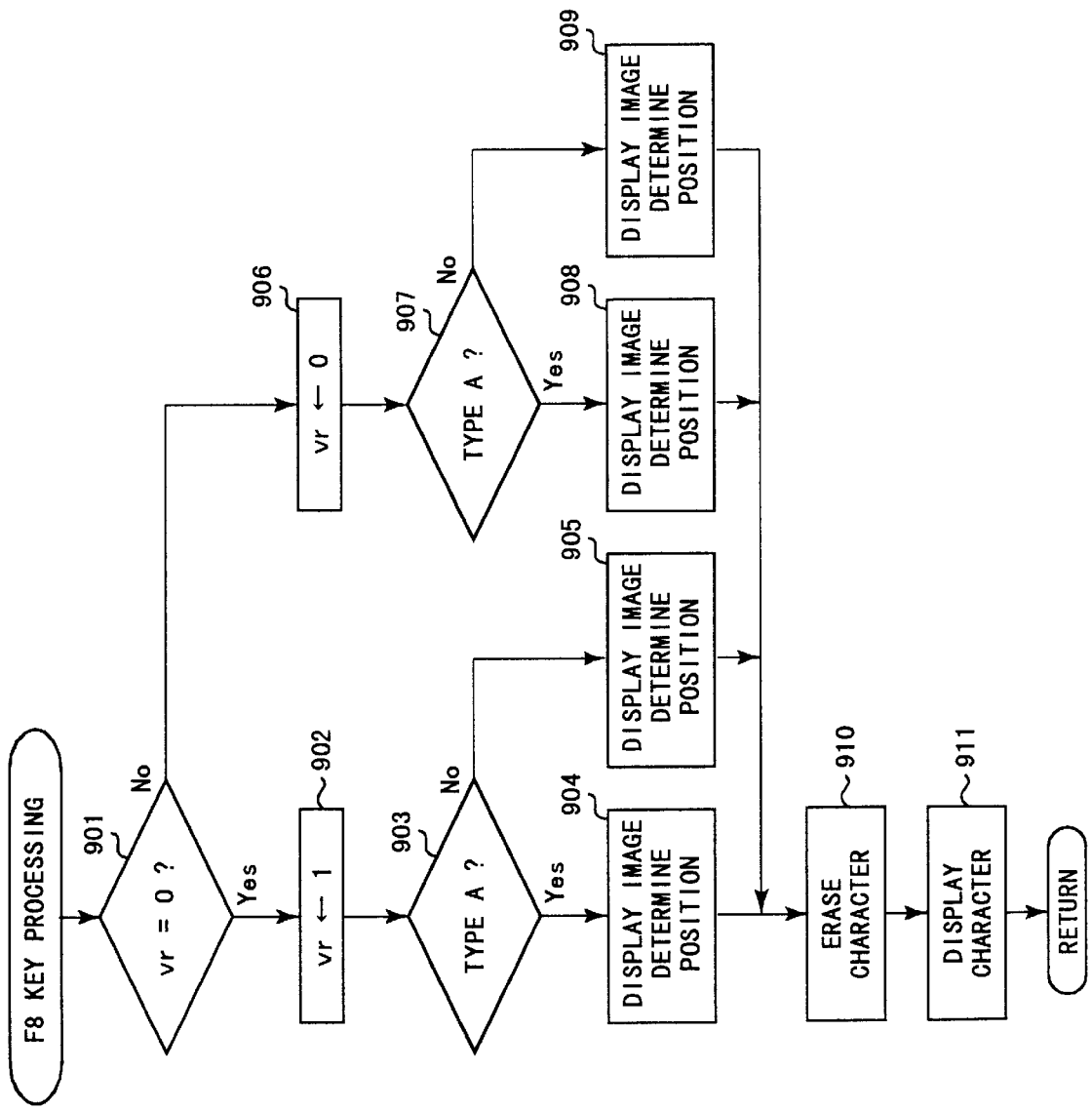
FIG. 14 is a view showing a subroutine of Steps 413 and 426 in FIG. 9.

FIG. 14 is a subroutine of Steps 413 and 426 in FIG. 9. As described above, this subroutine is performed when the F8 key 52 is depressed.

In Step 901, it is determined whether or not the display variable vr is 0, namely, whether the F8 key 52 on the keyboard 26 is depressed when the display-state is the normal-display. When it is determined that the display variable vr is 0, the process goes to Step 902.

In Step 902, the display variable vr is set to 1, namely, the display-state is changed to the magnification-display. Then, the process proceeds to Step 903.

In Step 903, it is determined whether or not the type A of the video-scope 10 is connected to the video-processor 20. When it is determined that the type A of the video-scope 10 is connected to the video-processor 20, the process goes to Step 904.

In Step 904, the object image is displayed within the magnifying image-area IA', as shown in the picture P1' of FIG. 2. Further, the x-y coordinates (x,y) of the character information are determined on the basis of the reference table T. Namely, the x-y coordinates (x,y), corresponding to the type A of the video-scope 10 and the magnification-display, are read from the array h, and then temporarily stored in the array H. In this case, the x-y coordinates (x,y) are:

$$(x,y)=(h[cp,3],h[cp,4]) \qquad (16)$$

The above x-y coordinates (x,y) are temporarily stored in the array H [cp,1] and the array H [cp,2]. Then, the process proceeds to Step 910.

On the other hand, when it is determined that the type B of the video-scope 10 is connected to the video-processor 20 at Step 903, the process goes to Step 905.

In Step 905, the object image is displayed within the magnifying image-area IB', as shown in the picture P2' of FIG. 2. Further, the x-y coordinates (x,y) of the character information are determined on the basis of the reference table T. Namely, the x-y coordinates (x,y), corresponding to the type B of the video-scope 10 and the magnification-display, are read from the array h, and then temporarily stored in the array H. In this case, the x-y coordinates (x,y) are:

$$(x,y)=(h[cp,7],h[cp,8]) \qquad (17)$$

The above x-y coordinates (x,y) are temporarily stored in the array H [cp,1] and the array H [cp,2]. Then, the process proceeds to Step 910.

When it is determined that the display variable vr is 1 at Step 901, namely, whether the F8 key 52 on the keyboard 26 is depressed when the display-state is the magnification-display (vr=1), the process goes to Step 906.

In Step 906, the display variable vr is set to 0, namely, the display-state is changed to the normal-display. Then, the process proceeds to Step 907.

In Step 907, it is determined whether or not type A of the video-scope 10 is connected to the video-processor 20. When it is determined that the type A of the video-scope 10 is connected to the video-processor 20, the process goes to Step 908.

In Step 908, the object image is displayed within the normal image-area IA, as shown in the picture P1 of FIG. 2. Further, the x-y coordinates (x,y) of the character information are determined on the basis of the reference table T. Namely, the x-y coordinates (x,y), corresponding to the type A of the video-scope 10 and the normal-display, are read from the array h , and then temporarily stored in the array H. In this case, the x-y coordinates (x,y) are:

$$(x,y)=(h[cp,1],h[cp,2]) \qquad (18)$$

The above x-y coordinates (x,y) are temporarily stored in the array H [cp,1] and the H [cp,2]. Then, the process proceeds to Step 910.

On the other hand, when it is determined that the type A of the video-scope 10 is not connected to the video-processor 20 at Step 907, the process goes to Step 909.

In Step 909, the object image is displayed within the normal image-area IB, as shown in the picture P2 of FIG. 2. Further, the x-y coordinates (x,y) are determined on the basis of the reference table T. Namely, the x-y coordinates (x,y), corresponding to the type B of the video-scope 10 and the normal-display, are read from the array h, and then temporarily stored in the array H. In this case, the x-y coordinates (x,y) are:

$$(x,y)=(h[cp,5],h[cp,6]) \qquad (19)$$

The above x-y coordinates (x,y) are temporarily stored in the array H[cp,1] and the array H [cp,2]. Then, the process proceeds to Step 910.

In Step 910, all of the character information, displayed on the screen W before the depression of the F8 key 52, is erased from the screen W. Then, at Step 911, each of the character information is newly displayed at the determined position in accordance with the x-y coordinates (x,y), set at one of Step 904, Step 905, Step 908 and Step 909. After the character information is newly displayed, this subroutine is terminated.

Figure 15:
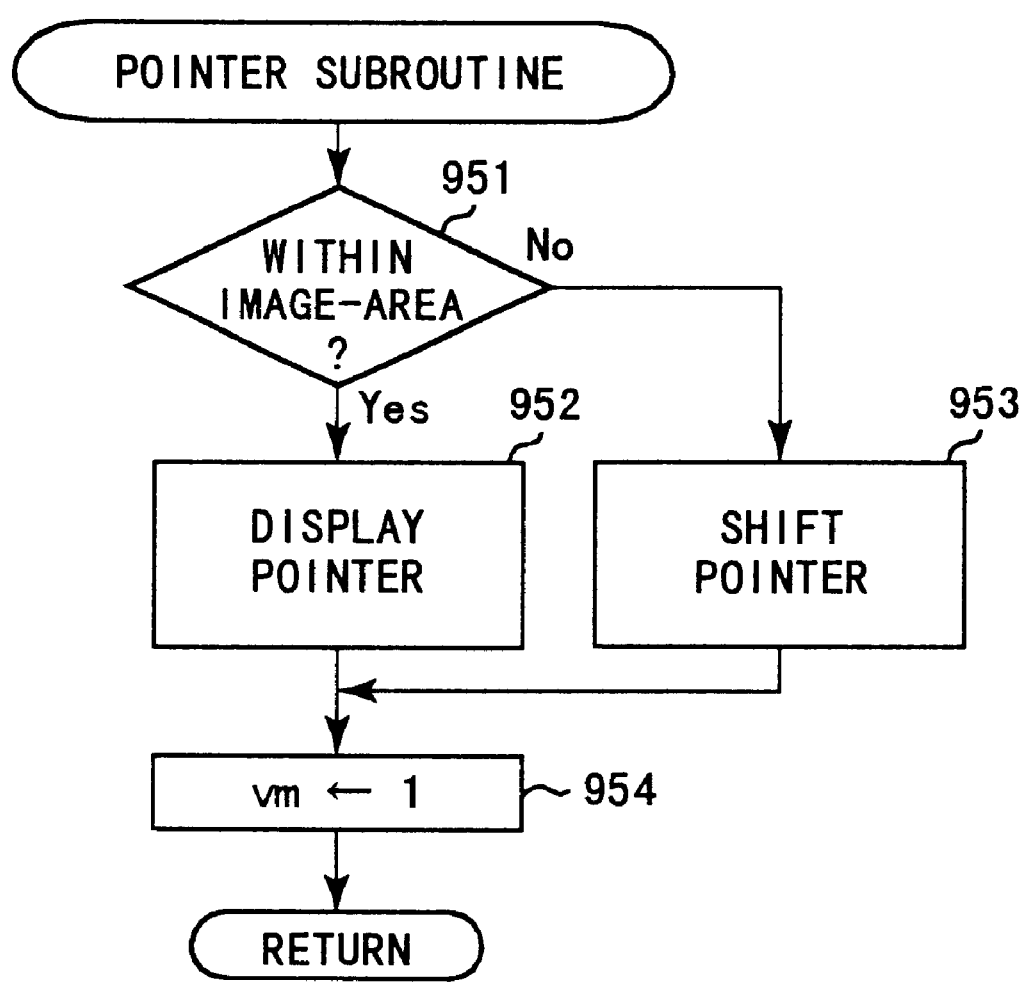
FIG. 15 is a view showing a sub routine of Steps 411 and 426 in FIG. 9, and further Step 103 in FIG. 5.

FIG. 15 is a subroutine of Step 411 in FIG. .9.

This subroutine is performed when the F4 key 53 is depressed. Further, this subroutine is also performed when Step 426 in FIG. 9 and Step 103 in FIG. 5 are performed. Namely, Steps 951 to 954 are performed when the exchange of the video-scope 10 is performed or when the change of the image-area is executed. Herein, the subroutine is referred to as "pointer subroutine".

At Step 951, it is determined whether or not the pointer P can be displayed within the image-area. Namely, it is determined whether or not a display-position, at which the pointer P is displayed before the erasing by the F4 key 53, the exchange of the video-scope or the change of the image-area, is within the image-area. Step 951 is performed on the basis of the x-y coordinates (x,y) stored in the array H[9,1], the array H[9,2] and the array H [10,1], the array H[10,2].

When it is determined that the pointer P can be displayed within the image-area, the process goes to Step 952, wherein the pointer P is displayed as before. Then, the process proceeds to Step 954.

On the other hand, when it is determined that the pointer P cannot be displayed within the image-area at Step 951, the display-position of the pointer P is changed such that the pointer P can be displayed within the image-area, at Step 953.

For example, when the magnification-display is changed to the normal-display by depressing the F8 key 52 when the type B of the video-scope 10 is connected to the video-processor 20 and the pointer P is displayed at a position of (28,15), within in the image-area IB', Step 951 is performed on the basis of the x-y coordinates (x,y) stored in the array H[9,1], the array H[9,2] and the array H[10,1], the array H[10,2], corresponding to the x-y coordinates (x,y) stored in the array h[9,5], the array h[9,6] and the array h[10,5], the array h[10,6] (See FIG. 4). As the display-position of (28,15) is beyond the normal-image-area IB, the pointer P is shifted to a position of (21,15) on the basis of the x-coordinate "21"stored in the array H [10,1], so that the pointer P is displayed on the boundary of the image-area IB. After the pointer P is shifted at Step 953, the process goes to Step 954.

In Step 954, the pointer display variable vm is set to 1, which indicates that the pointer P is displayed, and then the pointer subroutine is terminated.

As described above, the display-positions of the character information and the pointer P are adjusted in accordance with the size-change of the image-area. The display-positions of the character information are adjusted in accordance with the exchange of the video-scope, as shown at Steps 301 to 312 in FIG. 8, and in accordance with the size-change of the image-area, as shown at Steps 901 to 911 in FIG. 14. Also, the display-position of the pointer P is adjusted as shown at Steps 951 to 954 in FIG. 15.

Generally, in the conventional electronic endoscope, when the display-position of each item is determined, processing, which determines the type of the video-scope and determines whether the display-state is the normal-display or the magnification-display, is performed for each item, one by one. For example, after the display-position of the patient's name CH1 is determined by performing the above process, the display-position of the ID number CH2 is determined by performing the processing, similarly to the patient's name CH1.

On the other hand, in this embodiment, the display-positions of the character information (all of items) and the pointer P are determined from the reference table T. At this time, the corresponding x-y coordinates (x,y) of the character information and the pointer P, stored in the array h (ROM 33), are read and then temporarily stored in the array H (RAM 34). Thus, each item of the character information is displayed in accordance with the x-y coordinates (x,y) stored in the array H, and further the display-position of the pointer P is adjusted on the basis of the x-y coordinates (x,y) stored in the array H. Namely, the character information and the pointer P can be displayed without performing a processing, which determines the type of the video-scope 10 and further determines the display-state by each item. As a consequence, the processing-speed regarding a displaying of the character information and the pointer P improves.

As described above, generally, when the display-state is the magnification-display, the number of letters, which can be displayed in each column on the screen W, of the type A of the video-scope 10 is different from that of the type B of the video-scope 10. Namely, the x-y coordinates (x,y) of the character information and the pointer P are different depending upon the type of the video-scope 10 in a case where the display-state is the magnification-display. Accordingly, when the input of the letter and the shifting of the position of the cursor C and the pointer P are performed, the x-y coordinates (x,y) of the inputted letter, the cursor C and the pointer P are different depending upon the type of the video-scope 10. Therefore, conventionally, the type of the video-scope 10 is determined and the display-state is determined every time the letter is newly rewritten, the cursor C is shifted, or the pointer P is shifted.

However, in this embodiment, when the input of the letter and the shifting of the position of the cursor C and the pointer P are performed, the x-y coordinates (x,y) of the character information and the pointer P, corresponding to the image-area selected by the operator, is stored in the RAM 34, in short, the array H. Thus, the input of the letter and the shifting of the position of the cursor C and the pointer P are performed without performing the processing, which determines the type of the video-scope 10 and determines the display-state.

In a modification, only character information may be displayed on the basis of the reference table T.

Finally, it will be understood by those skilled in the art that the foregoing description is of preferred embodiment of the device, and that various changes and modifications may be made to the present invention without departing from the spirit and scope thereof.

The present disclosure relates to subject matters contained in Japanese Patent Application No. 10-370172 (filed on Dec. 25, 1998) which is expressly incorporated herein, by reference, in its entirety.

What is claimed is:

1. An electronic endoscope comprising:
   a video-scope having an image sensor provided at a distal end thereof, adapted to form an object image and generate image-pixel signals corresponding to said object image;
   a video-processor adapted to process said image-pixel signals so as to generate video signals, to which a proximal end of said video-scope and a monitor for displaying said object image are connected respectively;
   a character and mark generation controller adapted to generate character signals and indicator-mark signals, and further adapted to feed said character signals and said indicator-mark signals with said video signals to said monitor, such that character information and an indicator-mark are respectively displayed at a position on a screen of said monitor with said object image; and
   an image-area changer adapted to change a size of an image-area of said object image displayed on the screen of said monitor to another size, whereby said object image is selectively displayed within one of plural image-areas on the screen in accordance with a size-change of the image-area,
   wherein said character and mark generation controller includes a display-position adjuster adapted to determine display-positions of said character information and said indicator-mark on the basis of a reference table, in which a correspondence relationship between each of said image-areas and each of said display-positions of said character information and said indicator-mark is indicated, whereby said character information and said indicator-mark are respectively displayed at said determined display-positions in accordance with the size-change of said image-area.

2. The electronic endoscope of claim 1, wherein said display-position adjuster is further adapted to determine display-positions of said character information such that said character information is displayed beyond said image-area in accordance with the size-change of the image-area.

3. The electronic endoscope of claim 1, wherein said display-position adjuster is further adapted to determine a display-position of said indicator-mark such that said indicator-mark is displayed within said image-area in accordance with the size-change of the image-area.

4. The electronic endoscope of claim 1, wherein said image-area changer is adapted to change a normal image-area of said object image, which has a size corresponding to a number of pixels of said image sensor, to a magnifying image-area, which has a larger size compared with said normal image-area, and wherein said image-area changer is further adapted to change said magnifying image-area to said normal image-area.

5. The electronic endoscope of claim 4, wherein the size of said normal image-area differs depending upon a type of said video-scope connected to said video-processor.

6. The electronic endoscope of claim 5, wherein said reference table represents said display-positions of said character information corresponding to said normal image-area and said magnifying image-area of each type of said video-scope, and further represents limited-positions of said indicator-mark, which indicate a position on a corner of the image-area corresponding to said normal image-area and said magnifying image-area of each type of said video-scope.

7. The electronic endoscope of claim 6, wherein said display-positions of said character information and said indicator-mark are represented by x-y coordinates defined with respect to the screen of said monitor.

8. The electronic endoscope of claim 6, wherein said reference table indicates display-positions of a head letter in said character information.

9. The electronic endoscope of claim 6, further comprising a nonvolatile memory, in which said reference table is adapted to be stored as data in advance, and a volatile memory, in which said display-positions of said character information and said limited-positions of said indicator-mark are adapted to be temporarily stored.

10. The electronic endoscope of claim 9, wherein said display-position adjuster includes:
   a scope-type discriminator adapted to discriminate a type of said video-scope connected to said video-processor; and
   an image-area determiner adapted to determine whether said image area of said object image displayed on the screen is said normal image-area or said magnifying image-area, said display-position adjuster determining said display-positions of said character information and said limited-position of said indicator-mark, corresponding to the type of said video-scope connected to said video-processor and the image-area of said object image displayed on the screen, from said reference table stored in said nonvolatile memory.

11. The electronic endoscope of claim 10, wherein said display-position adjuster is adapted to read said determined display-positions of said character information and said determined limited-positions of said indicator-mark from said nonvolatile memory, and is further adapted to subsequently temporarily store said determined display-positions of said character information and said limited-positions of said indicator-mark in said volatile memory.

12. The electronic endoscope of claim 11, wherein said character and mark generation controller is adapted to feed said character signals to said monitor in accordance with said display-positions of said character information stored in said volatile memory.

13. The electronic endoscope of claim 11, wherein said display-position adjuster includes:
   a limited-position determiner adapted to determine whether said display-position of said indicator-mark before the change of the image-area is within the changed image-area on the basis of said stored limited-positions of said indicator-mark, said display-position adjuster adapted to determine said display-position of said indicator-mark to a boundary position of the changed image-area when said indicator-mark is displayed beyond the changed image-area.

14. The electronic endoscope of claim 10, wherein an input of a letter in said character information, a shifting of said display-position of said indicator-mark and a shifting of a cursor displayed on the screen are performed on the basis of said display-positions of said character information and said pointer stored in said volatile memory.

15. The electronic endoscope of claim 1, wherein said character information is information associated with said object image displayed on the screen of said monitor.

16. The electronic endoscope of claim 1, wherein said indicator-mark is a pointer for pointing to a specific portion in said image-area.

17. An electronic endoscope comprising:
   a video-scope having an image sensor provided at a distal end thereof, adapted to form an object image and generate image-pixel signals corresponding to said object image;
   a video-processor adapted to process said image-pixel signals so as to generate video signals, to which a proximal end of said video-scope and a monitor for displaying said object image are connected respectively;
   a character generation controller adapted to generate character signals, and further adapted to feed said character signals with said video signals to said monitor, such that character information is displayed at a position on a screen of said monitor with said object image; and
   an image-area changer adapted to change a size of an image-area of said object image displayed on the screen of said monitor to another size, whereby said object image is selectively displayed within one of plural image-areas on the screen in accordance with a size-change of the image-area,
      wherein said character generation controller includes a display-position adjuster adapted to determine display-positions of said character information on the basis of a reference table, in which a correspondence relationship between each of said image-areas and each of said display-positions of said character information is indicated, whereby said character information is displayed at said determined display-positions in accordance with the size-change of said image-area.

18. A video-processor of an electronic endoscope, to which a proximal end of a video-scope and a monitor for displaying an object image are adapted to be connected respectively, said video-scope having an image sensor adapted to form an object image and generate image-pixel signals corresponding to said object image, said video-processor processing said image-pixel signals so as to generate video signals to feed said video-signals to said monitor, said video-processor comprising:
   a character generation controller adapted to generate character signals, and further adapted to feed said character signals with said video signals to said monitor, such that character information is displayed at a position on a screen of said monitor with said object image; and
   an image-area changer adapted to change a size of an image-area of said object image displayed on the screen of said monitor to another size, whereby said object image is selectively displayed within one of plural image-areas on the screen in accordance with a size-change of the image-area,
      wherein said character generation controller includes a display-position adjuster adapted to determine display-positions of said character information on the basis of a reference table, in which a correspondence relationship between each of said image-areas and each of said display-positions of said character information is indicated, whereby said character information is displayed at said determined display-positions in accordance with the size-change of said image-area.

19. An electronic endoscope system comprising:

a video-scope having an image sensor provided at a distal end thereof, and adapted to form an object image and generate image-pixel signals corresponding to said object image;

a video-processor adapted to process said image-pixel signals so as to generate video signals, to which a proximal end of said video-scope is connected;

a monitor connected to said video-processor, adapted to display said object image;

a character generation controller adapted to generate character signals, and further adapted to feed said character signals with said video signals to said monitor, such that character information is displayed at a position on a screen of said monitor with said object image; and an image-area changer adapted to change a size of an image-area of said object image displayed on the screen of said monitor to another size, whereby said object image is selectively displayed within one of plural image-areas on the screen in accordance with a size-change of the image-area, wherein said character generation controller includes a display-position adjuster adapted to determine display-positions of said character information on the basis of a reference table, in which a correspondence relationship between each of said image-areas and each of said display-positions of said character information is indicated, whereby said character information is displayed at said determined display-positions in accordance with the size-change of said image-area.

* * * * *